(12) United States Patent
Khieu et al.

(10) Patent No.: US 10,675,449 B2
(45) Date of Patent: Jun. 9, 2020

(54) HIGH PRESSURE BALLOON

(71) Applicant: BOSTON SCIENTIFIC SCIMED, INC., Maple Grove, MN (US)

(72) Inventors: Aaron Khieu, Maple Grove, MN (US); John Jianhua Chen, Plymouth, MN (US); Ying Xiong, Maplewood, MN (US); Joe Khammoungkhoune, St. Michael, MN (US); Daniel James Horn, Shoreview, MN (US); John Blix, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 16/145,421

(22) Filed: Sep. 28, 2018

(65) Prior Publication Data

US 2019/0030301 A1    Jan. 31, 2019

Related U.S. Application Data

(60) Continuation of application No. 15/354,436, filed on Nov. 17, 2016, now Pat. No. 10,099,039, which is a
(Continued)

(51) Int. Cl.
*A61M 25/10* (2013.01)
*B32B 5/02* (2006.01)
(Continued)

(52) U.S. Cl.
CPC .......... *A61M 25/10* (2013.01); *A61L 29/049* (2013.01); *A61L 29/14* (2013.01); *A61L 29/143* (2013.01); *A61M 25/1002* (2013.01); *A61M 25/104* (2013.01); *A61M 25/1029* (2013.01); *B32B 1/02* (2013.01); *B32B 5/02* (2013.01); *B32B 5/22* (2013.01); *B32B 5/24* (2013.01); *B32B 5/28* (2013.01); *C08L 23/06* (2013.01); *C08L 75/04* (2013.01); *C08L 77/00* (2013.01);
(Continued)

(58) Field of Classification Search
CPC .............. A61M 25/10; A61M 25/1029; A61M 25/104; A61M 2025/1075; A61M 2025/1084; B32B 1/02; B32B 5/02; B32B 5/22; B32B 5/24; B32B 5/28; Y10T 428/1334; Y10T 428/1366
See application file for complete search history.

(56) References Cited

U.S. PATENT DOCUMENTS 4,702,252 A    10/1987    Brooks et al.
4,706,670 A    11/1987    Andersen et al.
(Continued)

FOREIGN PATENT DOCUMENTS

EP    0540858 A1    5/1993
EP    0553960 A1    8/1993
(Continued)

*Primary Examiner* — Walter Aughenbaugh
(74) *Attorney, Agent, or Firm* — Seager, Tufte & Wickhem LLP

(57) ABSTRACT

Composite fiber reinforced balloons for medical devices are prepared by applying a web of fibers to the exterior of a preformed underlayer balloon, encasing the web with a matrix material to form an assembly, and inserting the assembly into a preformed outer layer balloon to form the composite balloon.

17 Claims, 5 Drawing Sheets

Related U.S. Application Data continuation of application No. 14/843,564, filed on Sep. 2, 2015, now Pat. No. 9,526,873, which is a continuation of application No. 14/494,894, filed on Sep. 24, 2014, now Pat. No. 9,144,666, which is a continuation of application No. 13/735,111, filed on Jan. 7, 2013, now Pat. No. 8,697,212, which is a division of application No. 13/247,628, filed on Sep. 28, 2011, now Pat. No. 8,349,237, which is a continuation of application No. 11/407,576, filed on Apr. 20, 2006, now Pat. No. 8,858,855.

(51) Int. Cl.

| | | |
|---|---|---|
| *B32B 1/02* | (2006.01) | |
| *B32B 5/28* | (2006.01) | |
| *B32B 5/22* | (2006.01) | |
| *B32B 5/24* | (2006.01) | |
| *A61L 29/04* | (2006.01) | |
| *A61L 29/14* | (2006.01) | |
| *C08L 23/06* | (2006.01) | |
| *C08L 75/04* | (2006.01) | |
| *C08L 77/00* | (2006.01) | |

(52) U.S. Cl.
CPC ............... *A61M 2025/1075* (2013.01); *A61M 2025/1084* (2013.01); *A61M 2025/1088* (2013.01); *A61M 2205/0216* (2013.01); *Y10T 428/1334* (2015.01); *Y10T 428/1352* (2015.01); *Y10T 428/1362* (2015.01); *Y10T 428/1366* (2015.01); *Y10T 428/1372* (2015.01); *Y10T 428/1386* (2015.01)

(56) References Cited

U.S. PATENT DOCUMENTS

| | | |
|---|---|---|
| 4,896,669 A | 1/1990 | Bhate et al. |
| 4,906,244 A | 3/1990 | Pinchuk et al. |
| 4,906,422 A | 3/1990 | Buckley |
| 4,935,190 A | 6/1990 | Tennerstedt |
| 4,950,239 A | 8/1990 | Gahara et al. |
| 4,963,313 A | 10/1990 | Noddin et al. |
| 5,026,607 A | 6/1991 | Kiezulas |
| 5,096,848 A | 3/1992 | Kawamura |
| 5,135,516 A | 8/1992 | Sahatjian et al. |
| 5,201,706 A | 4/1993 | Noguchi et al. |
| 5,250,069 A | 10/1993 | Nobuyoshi et al. |
| 5,270,086 A | 12/1993 | Hamlin |
| 5,304,121 A | 4/1994 | Sahatjian |
| 5,304,340 A | 4/1994 | Downey |
| 5,306,246 A | 4/1994 | Sahatjian et al. |
| 5,328,468 A | 7/1994 | Kaneko et al. |
| 5,330,428 A | 7/1994 | Wang et al. |
| 5,330,429 A | 7/1994 | Noguchi et al. |
| 5,338,299 A | 8/1994 | Barlow |
| 5,344,400 A | 9/1994 | Kaneko et al. |
| 5,348,538 A | 9/1994 | Wang et al. |
| 5,403,340 A | 4/1995 | Wang et al. |
| 5,500,180 A | 3/1996 | Anderson et al. |
| 5,503,631 A | 4/1996 | Onishi et al. |
| 5,509,899 A | 4/1996 | Fan et al. |
| 5,556,383 A | 9/1996 | Wang et al. |
| 5,576,072 A | 11/1996 | Hostettler et al. |
| 5,578,374 A | 11/1996 | Dunbar et al. |
| 5,647,848 A | 7/1997 | Jorgensen |
| 5,693,034 A | 12/1997 | Buscemi et al. |
| 5,702,754 A | 12/1997 | Zhong |
| 5,702,756 A | 12/1997 | McKean et al. |
| 5,714,110 A | 2/1998 | Wang et al. |
| 5,755,690 A | 5/1998 | Saab |
| 5,772,681 A | 6/1998 | Leoni |
| 5,797,877 A | 8/1998 | Hamilton et al. |
| 5,827,289 A | 10/1998 | Reiley et al. |
| 5,828,289 A | 10/1998 | Burgess |
| 5,833,657 A | 11/1998 | Reinhardt et al. |
| 5,958,582 A | 9/1999 | Dunbar et al. |
| 5,985,582 A | 11/1999 | Triscott |
| 6,024,722 A | 2/2000 | Rau et al. |
| 6,110,483 A | 8/2000 | Whitbourne et al. |
| 6,146,356 A | 11/2000 | Wang et al. |
| 6,156,254 A | 12/2000 | Andrews et al. |
| 6,270,522 B1 | 8/2001 | Simhambhatla et al. |
| 6,394,998 B1 | 5/2002 | Wallace et al. |
| 6,528,150 B2 | 3/2003 | Nazarova et al. |
| 6,572,813 B1 | 6/2003 | Zhang et al. |
| 6,673,053 B2 | 1/2004 | Wang et al. |
| 6,723,267 B2 | 4/2004 | Simmelink et al. |
| 6,746,425 B1 | 6/2004 | Beckham |
| 6,977,103 B2 | 12/2005 | Chen et al. |
| 7,029,732 B2 | 4/2006 | Wang et al. |
| 7,635,510 B2 * | 12/2009 | Horn ............... A61L 29/126 428/34.1 |
| 7,943,221 B2 | 5/2011 | Horn et al. |
| 8,697,212 B2 | 4/2014 | Khieu et al. |
| 9,144,666 B2 | 9/2015 | Khieu et al. |
| 2002/0049402 A1 | 4/2002 | Peacock, III et al. |
| 2002/0198492 A1 | 12/2002 | Miller et al. |
| 2003/0143350 A1 | 7/2003 | Jimenez |
| 2004/0082965 A1 | 4/2004 | Beckham |
| 2004/0109964 A1 | 6/2004 | Beckham |
| 2005/0015046 A1 | 1/2005 | Weber et al. |
| 2005/0123702 A1 | 6/2005 | Beckham |
| 2005/0271844 A1 | 12/2005 | Mapes et al. |
| 2006/0008606 A1 | 1/2006 | Horn et al. |
| 2006/0085024 A1 | 4/2006 | Pepper et al. |
| 2007/0250101 A1 | 10/2007 | Horn et al. |
| 2007/0267128 A1 | 11/2007 | Horn et al. |

FOREIGN PATENT DOCUMENTS

| | | |
|---|---|---|
| GB | 2130093 A | 5/1984 |
| WO | 9803218 A1 | 1/1998 |
| WO | 9805377 A1 | 2/1998 |
| WO | 02068011 A1 | 9/2002 |
| WO | 2005072804 A1 | 8/2005 |
| WO | 2006016934 A1 | 2/2006 |
| WO | 2006086516 A2 | 8/2006 |
| WO | 2007037821 A1 | 4/2007 |

\* cited by examiner

HIGH PRESSURE BALLOON

CROSS-REFERENCE TO RELATED APPLICATIONS

This application is a Continuation of U.S. patent application Ser. No. 15/354,436, filed on Nov. 17, 2016, which is a Continuation of U.S. patent application Ser. No. 14/843,564, filed on Sep. 2, 2015, issued as U.S. Pat. No. 9,526,873, on Dec. 27, 2016, which is a Continuation of U.S. patent application Ser. No. 14/494,894, filed on Sep. 24, 2014, issued as U.S. Pat. No. 9,144,666, on Sep. 29, 2015, which is a Continuation of U.S. patent application Ser. No. 13/735,111, filed on Jan. 7, 2013, issued as U.S. Pat. No. 8,697,212, on Apr. 15, 2014, which is a Divisional of U.S. patent application Ser. No. 13/247,628, filed on Sep. 28, 2011, issued as U.S. Pat. No. 8,349,237, on Jan. 8, 2013, which is a Continuation of U.S. application Ser. No. 11/407,576, filed on Apr. 20, 2006, issued as U.S. Pat. No. 8,858,855, on Oct. 14, 2014 the contents of which are hereby incorporated herein by reference.

BACKGROUND OF THE INVENTION

Medical devices comprising catheter shafts and catheter balloons are used in an increasingly widening variety of applications including vascular dilatation, stent delivery, drug delivery, delivery and operation of sensors and surgical devices such as blades, and the like. The desired physical property profile for the balloons used in these devices varies according to the specific application, but for many applications a high strength robust balloon is necessary and good softness and trackability properties are highly desirable.

Commercial high strength balloons having wall strengths in excess of 20,000 psi have been formed of a wide variety of polymeric materials, including PET, nylons, polyurethanes and various block copolymer thermoplastic elastomers. A particular application which has a very high pressure requirement is reopening of stenoses which develop at or in long-term shunt, ports or grafts employed for repeated blood access, for instance with dialysis patients. Such stenoses are often highly calcified and essentially must be subjected to very high pressure for successful treatment. Moreover, frequently the vessels into which the access devices are connected are quite large. Consequently there is a need for balloons whose pressure profile allows for use of pressures in excess of 20 atm at balloon diameters which can exceed 5 mm.

Documents relating to fiber reinforced medical balloons include U.S. Pat. No. 4,896,669, Behate; U.S. Pat. No. 4,706,670, Andersen; U.S. Pat. No. 5,647,848, Jorgensen; U.S. Pat. No. 5,201,706, and U.S. Pat. No. 5,330,429, Noguchi; U.S. Pat. No. 5,827,289, Reiley; and U.S. Pat. No. 6,156,254, Andrews.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. § 1.56(a) exists.

Without limiting the scope of the invention a brief summary of some of the claimed embodiments of the invention is set forth below. Additional details of the summarized embodiments of the invention and/or additional embodiments of the invention may be found in the Detailed Description of the Invention below.

SUMMARY OF THE INVENTION

The invention pertains to fiber reinforced laminate composite balloons and processes for preparing laminate composite balloons. Other aspects of the invention pertain more generally to composite fiber reinforced medical device balloons.

In one inventive aspect, the balloon comprises an underlying balloon layer, a fiber web disposed over the underlying balloon layer and a matrix material encasing the web.

In one inventive aspect, the balloon comprises an underlying balloon layer, a fiber web disposed over the underlying balloon layer, a matrix material encasing the web and an overlying balloon layer of radially oriented polymer material disposed over the fiber web and matrix material.

In some aspects the invention pertains to manufacturing processes for preparing composite fiber reinforced balloons. One such aspect of the method comprises:
providing a preformed underlayer balloon;
applying a web of fibers to the exterior of said underlayer balloon;
encasing the web with a matrix material to form an assembly of underlayer balloon and fiber matrix;
providing a preformed overlayer balloon;
inserting the assembly of underlayer balloon and fiber matrix into the preformed overlayer balloon form and bonding said assembly and overlayer balloon to form said composite fiber reinforced balloon.

In some embodiments, the invention pertains to balloons and manufacturing methods as described above wherein the balloon has a fiber matrix ratio, taken as the thickness of the intermediate fiber and matrix material to the total thickness of the balloon, in the range of about 0.51 to about 0.73.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described an embodiments of the invention.

DETAILED DESCRIPTION OF THE INVENTION

Figure 1:
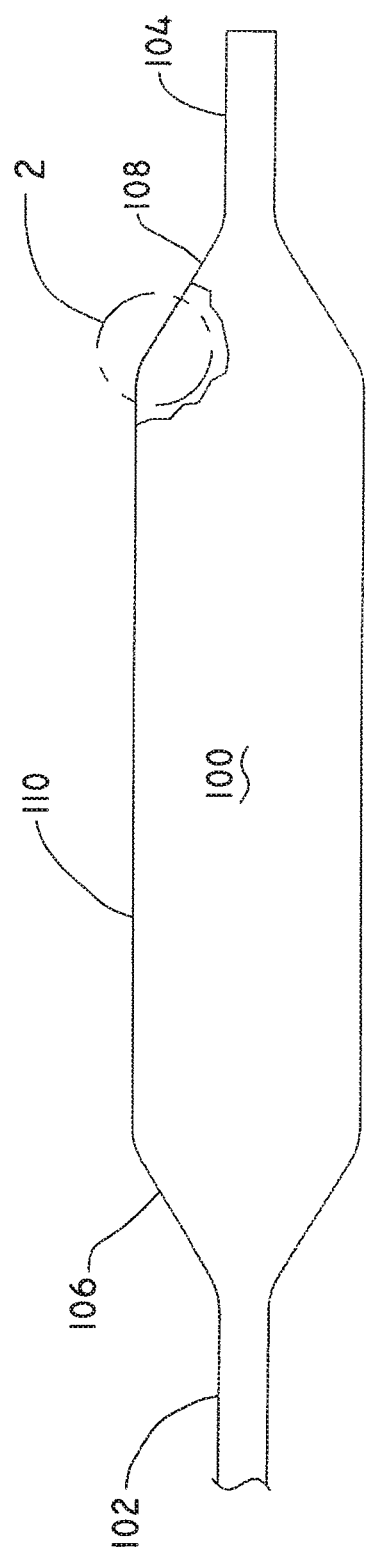
FIG. 1 is a schematic side view of an underlayer balloon with a partial cutaway.

All US patents and applications and all other published documents mentioned anywhere in this application are incorporated herein by reference in their entirety.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Balloons of the invention are particularly suited to use in medical devices, for instance on balloon angioplasty catheters, in stent delivery systems, perfusion balloon devices, cutting balloon devices, cryoplasty devices, and the like. Typically they will be mounted on a catheter or probe device.

Referring to the drawing FIGS. 1-5, several aspects of the inventive processes are illustrated.

Figure 2:
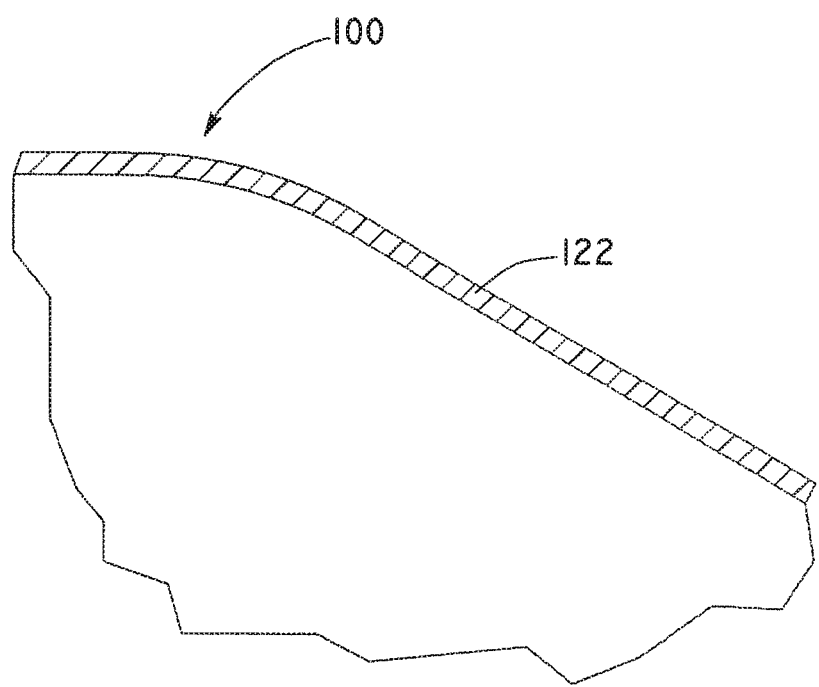
FIG. 2 is an enlarged cutaway view taken at line 2 of FIG. 1.

FIGS. 1 and 2 show an underlayer balloon 100 comprising waist regions 102, 104, cone regions 106, 108 and body region 110. The underlayer balloon 100 can be in one embodiment formed of a single layer 122 of a radially oriented thermoplastic polymer.

Figure 3:
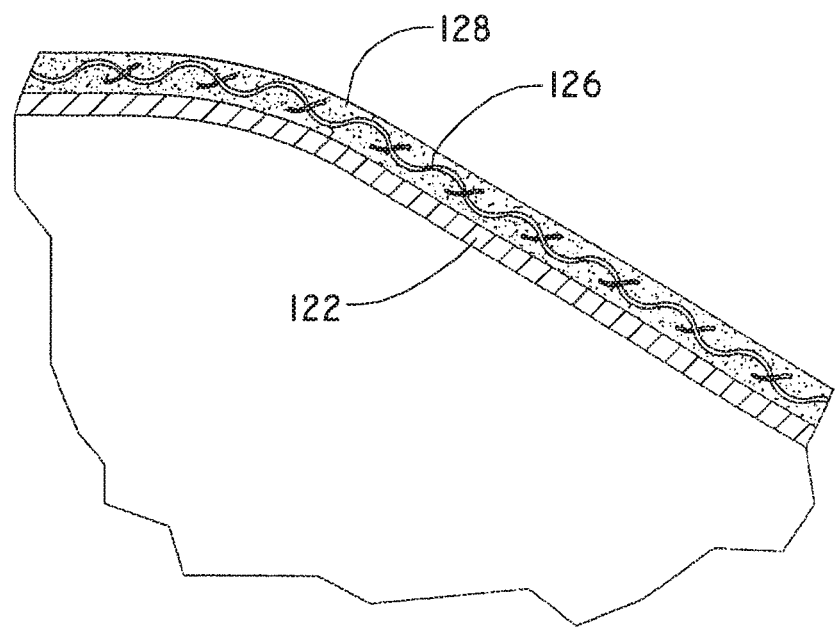
FIGS. 3 and 4 are views as in FIG. 2 illustrating steps of an embodiment of the inventive method.

FIG. 3 is a view as in FIG. 2, after application of a fiber web 126 and matrix material 128. The fiber web 126 is encased by the matrix material 128.

Figure 4:
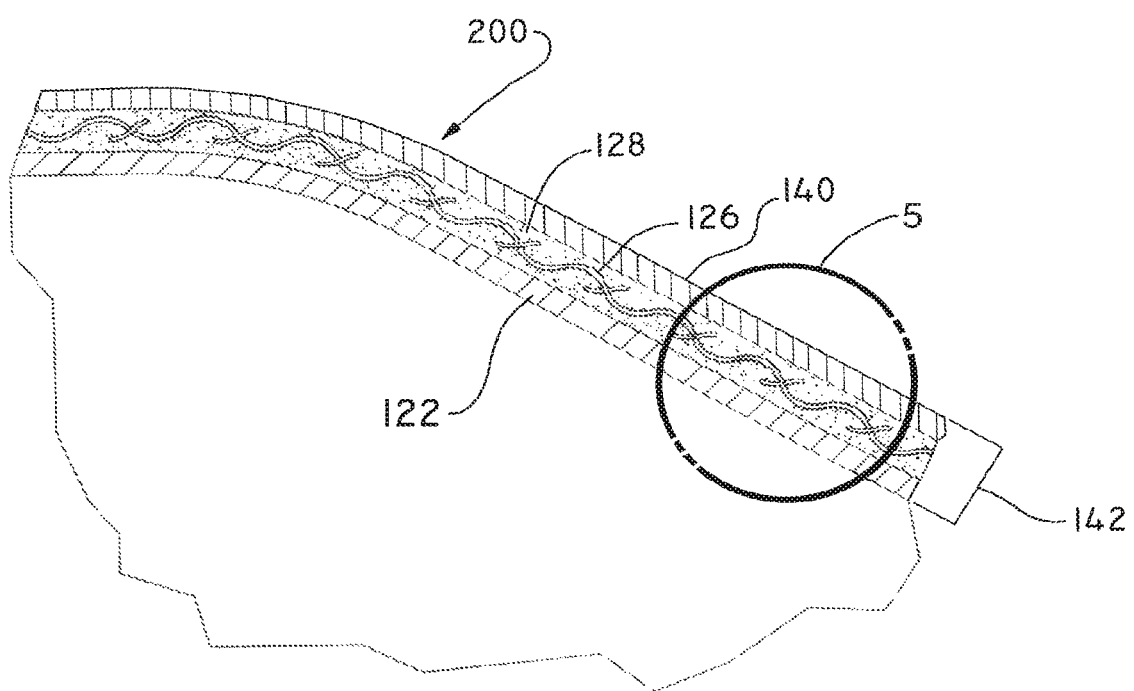

FIG. 4 is a view as in FIG. 3, after the application of an outerlayer balloon 140 to complete the composite balloon 200. The matrix material 28 and fiber web 126 are sandwiched between the layer 122 provided by the underlayer balloon and the layer 140 provided by the outerlayer balloon.

Figure 5:
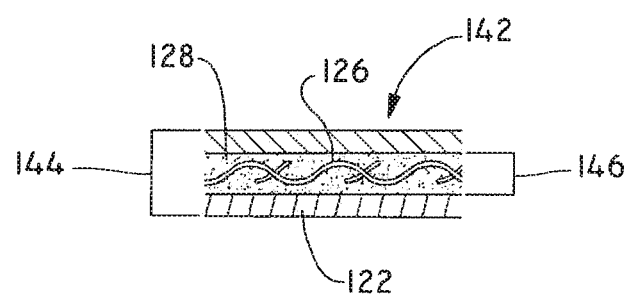
FIG. 5 is a cutaway view taken at line 5 of FIG. 4.

FIG. 5 is an isolated portion of the composite balloon wall 142 of the embodiment shown in FIG. 4.

Underlayer Balloon

In some aspects the invention pertains to a composite balloon, or method of forming same, in which a web material is formed from fibers by application over an underlayer balloon form that becomes part of the composite balloon.

The underlayer balloon may be preformed in a manner known for forming medical device balloons. For instance, a tubular parison of a semi-crystalline polymeric material may be radially expanded, or radially expanded with longitudinal stretching to form the underlayer balloon. Optionally the underlayer balloon may be still further processed before it is incorporated into the composite balloon. The extruded parison used to prepare the underlayer balloon may be radially expanded into a mold or by free-blowing. Alternatively, the parison may be pre-stretched longitudinally before expansion or reformed in various ways to reduce thickness of the balloon cone and waist regions prior to radial expansion. The blowing process may utilize pressurization under tension, followed by rapid dipping into a heated fluid; a sequential dipping with differing pressurization; a pulsed pressurization with compressible or incompressible fluid, after the material has been heated. Heating may also be accomplished by heating the pressurization fluid injected into the parison. Examples of these techniques may be found in the patent documents mentioned elsewhere in this application or in U.S. Pat. No. 4,963,313, U.S. Pat. No. 5,306,246, U.S. Pat. No. 4,935,190, U.S. Pat. No. 5,714,110 and U.S. Pat. No. 5,304,340. Various known methods of altering the properties of a radially expanded balloon such as heat-setting, heat shrinking, and/or radiation crosslinking may also be employed in forming the underlayer balloon. See U.S. Pat. No. 5,403,340; EP 540858; and WO 98/03218.

The underlayer balloon may be formed of any material which may be made by radial expansion of a tubular parison, typically thermoplastic polymers. Documents pertinent to materials which may be employed this way include U.S. Pat. No. 4,906,244, Pinchuk et al, and U.S. Pat. No. 5,328,468, Kaneko, which describe polyamide balloons; U.S. Pat. No. 4,950,239, Gahara, and U.S. Pat. No. 5,500,180, Anderson et al, which describe balloons made from polyurethane block copolymers; U.S. Pat. No. 5,556,383, Wang et al, and U.S. Pat. No. 6,146,356, Wang et al, which describe balloons made from polyether-block-amide copolymers and polyester-block-ether copolymers; U.S. Pat. No. 6,270,522, Simhambhatla, et al, which describes balloons made from polyester-block-ether copolymers of high flexural modulus; U.S. Pat. No. 5,344,400, Kaneko, which describes balloons made from polyarylene sulfide; and U.S. Pat. No. 5,833,657, Reinhart et al, which describes balloons having a layer of polyetheretherketone. U.S. Pat. No. 5,250,069, Nobuyoshi et al, U.S. Pat. No. 5,797,877, Hamilton et al, and U.S. Pat. No. 5,270,086, Hamlin, describe still further materials which may be used to make such balloons.

Such materials may include low, linear low, medium and high density polyethylenes; polypropylenes; poly(ethylene vinyl acetate) (EVA); poly(ethylene vinyl alcohol) (EVOH) and EVA/EVOH terpolymers; polyolefin-ionomers; ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; polyesters and copolyesters; polycarbonate; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); polyetheretherketone (PEEK) and PES (polyether sulfone). Physical blends and copolymers of such materials may also be used.

Orientable polymers are among the preferred materials for forming the underlayer balloon. Suitable orientable polymers include aromatic polyesters, especially polyethylene terephthalate (PET). PET polymers may have an initial intrinsic viscosity about 0.5 or more, for instance, 0.6-1.3. Other high strength polyester materials, such as poly(ethylene naphthalate) (PEN); and poly(butylene terephthalate) may also be used. Polyester copolymers incorporating ethylene terephthalate, ethylene naphthalate, butylene terephthalate and/or butylene naphthalate repeat units, may also be employed. Polyester copolymers such as the random copolymer made from dimethyl terephthalate dimethyl isophthalate and ethylene glycol described in U.S. Pat. No. 5,330,428 Wang, et al. may also be employed.

Examples of polyamides which may be used include nylon 6, nylon 64, nylon 66, nylon 610, nylon 610, nylon 612, nylon 46, nylon 9, nylon 10, nylon 11, nylon 12, and mixtures thereof.

The underlayer balloon may be formed of polyurethanes such as Tecothane® from Thermedics. Tecothane® is a thermoplastic, aromatic, polyether polyurethane synthesized from methylene diisocyanate (MDI), polytetramethylene ether glycol (PTMEG) and 1,4-butanediol chain extender. Tecothane® 1065D and 1075D are examples. Other polyurethanes that can be used include Isoplast® 301, a high strength engineering thermoplastic polyurethane, and Pellethane® 2363-75D, both sold by Dow Chemical Co. References illustrating polyurethane balloon materials include U.S. Pat. No. 4,950,239, to Gahara, U.S. Pat. No. 5,500,180 to Anderson et al, U.S. Pat. No. 6,146,356 to Wang, et al., and U.S. Pat. No. 6,572,813, to Zhang, et al.

Underlayer balloons may be also made of polyamide/polyether block copolymers. The polyamide/polyether block copolymers are commonly identified by the acronym PEBA (polyether block amide). The polyamide and polyether segments of these block copolymers may be linked through amide linkages, however, most preferred are ester linked segmented polymers, i.e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether.

Polyamide/polyether polyesters are sold commercially under the Pebax® trademark. Examples of suitable commercially available polymers are the Pebax® 33 series polymers with hardness 60 and above, Shore D scale, especially Pebax® 6333, 7033 and 7233. These polymers are made up of nylon 12 segments and poly(tetramethylene ether) segments linked by ester groups.

It is also possible to utilize polyester/polyether segmented block copolymers. Such polymers are made up of at least two polyester segments and at least two polyether segments. The polyether segments are the same as previously described for the polyamide/polyether block copolymers useful in the invention. The polyester segments are polyesters of an aromatic dicarboxylic acid and a two to four carbon diol.

The polyether segments of the polyester/polyether segmented block copolymers are aliphatic polyethers having at least 2 and no more than 10 linear saturated aliphatic carbon atoms between ether linkages. More preferably the ether segments have 4-6 carbons between ether linkages, and most preferably they are poly(tetramethylene ether) segments. Examples of other polyethers which may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 150 and 2,500, preferably between 250 and 1000.

The polyester segments of the polyester/polyether segmented block copolymers are polyesters of an aromatic dicarboxylic acid and a two to four carbon diol. Suitable dicarboxylic acids used to prepare the polyester segments of the polyester/polyether block copolymers are ortho-, meta- or para-phthalic acid, naphthalenedicarboxylic acid or meta-terphenyl-4,4'-dicarboxylic acids. Preferred polyester/polyether block copolymers are poly(butylene terephthalate)-block-poly(tetramethylene oxide) polymers such as Arnitel® EM 740, sold by DSM Engineering Plastics, and Hytrel® polymers, sold by DuPont, such as Hytrel® 8230.

A suitable thermoplastic polyimide is described in U.S. Pat. No. 5,096,848 and is available commercially under the tradename Aurum® from Mitsui Toatsu Chemicals, Inc., of Tokyo, Japan.

Examples of liquid crystal polymers include the products Vectra® from Hoechst Celanese; Rodrun® from Unitika; LX and HX series polymers and Zenite™ polymers from DuPont; Sumikosuper™ and Ekonol™ from Sumitomo Chemical; Granlar™ from Grandmont; and Xydar® from Amoco. Suitably the liquid crystal polymer materials when employed in the underlayer balloon are blended with another thermoplastic polymer such as PET, nylon 12, or a block copolymer such as Pebax® 7033 or 7233 or Arintel® EM 740 or Hytrel 8230. The liquid crystal polymer may be present as filaments in a matrix of the blend polymer.

Alternatively, the underlayer balloon may be obtained by polymerization of a curable composition on a mold form, for instance as described in commonly owned applications US 2005-0015046 A1, and/or US 2006-0008606 A1.

The underlayer balloon is formed at a thickness which will provide a sufficiently rigid profile upon inflation to a low pressure, for example 2-3 atm, to permit direct application of fibers thereto in a manner which forms a fiber web overlying the balloon. Preferably the underlayer balloon is substantially radially oriented or biaxially (radially and longitudinally) oriented. The underlayer balloon may have a wall thickness, single wall basis, of from about 5 µm to about 50 µm (0.0002-0.002 inches), for instance 8 to 30 µm (0.0003-0.0012 inches), suitably about 10 to about 25 µm (0.0004-0.0010 inches).

Fiber Web

Various techniques for forming webs are known. Suitable webs may be braids, weaves, mesh, helical windings, knits or random rovings. The web may be formed of different materials, for instance if anisotropic longitudinal lengthening and diameter expansion properties are desired.

The fiber selection and the web pattern can influence the distension properties of the composite balloon. Fiber tension during application to the underlayer balloon can also affect distension of the composite balloon, especially if elastomeric fibers are employed in whole or in part. In some preferred embodiments, however, the composite balloon is substantially non-distensible in both the longitudinal and radial directions, in which case the fibers have very low elongation, and the pattern is selected to provide minimal expansion. Weaves or braids are particularly desirable webforms in these embodiments. A circular braider may be employed to apply the fibers to the underlayer balloon.

The web pattern may provide crossing fibers at any angle. Typically at least one set of the fibers will wind helically around the circumference of the underlayer balloon. In at least some embodiments a set of longitudinal fibers is provided, running parallel to the longitudinal axis over at least a portion of the underlayer balloon. The longitudinal fibers may be inelastic. In some embodiments the longitudinal fibers are interwoven or braided into the web pattern with fibers that wind helically around the balloon, for instance, the helical fibers may cross over and under the longitudinal fibers in an individually or grouped alternating fashion to provide the weave or braid. Crossing fibers that run at several different angles may be used. For instance, longitudinal fibers may be crossed both by fibers running at 45° and at 135° thereto. In some embodiments, the braiding angle may be 68 to 70. Particularly with fiber webs produced using mechanical braiders, crossing angles that produce optimal reinforcement may not occur with optimal gap spacing between fiber crossings. Groupings of individual fibers may be employed to reduce gap spacing at any desired crossing angle. For instance, crossing groupings of 2-6 fibers by 2-6 fibers may give better results than 1×1 crossings. The groupings may have different sizes, for instance 2 (longitudinal) by 4 (45° helical) by 4 (135° helical).

The fibers may be monofilament or multifilament fibers. Any size which is suitable may be used. For example, in some embodiments, the fibers may range in size from 1 to 50 µm or in denier from 10-100. In some embodiments, the denier is from 25-50. Moreover, deviations from this size range can be achieved in some cases without departing from the invention.

Individual filaments in a multifilament fiber may have denier size less than 10, for instance from 1-5 denier. Larger filaments may also be employed in multifilament fibers. Multifilament fibers may be a blend of fibers of different materials.

The fiber material may be polyester, polyolefin, polyamide, polyurethane, liquid crystal polymer, polyimide, carbon, glass, mineral fiber or a combination thereof. Polyesters include polyethyleneterephthalate (PET), polybutylene terephthalate (PBT), and polytrimethylene terephthalate (PTT). Polyamides include nylons and aramids such as Kevlar®. Liquid crystal polymers include Vectran®. Polyolefins include ultrahigh molecular weight polyethylene, such as Dyneema,® sold by DSM Dyneema BVm Heerlen, Netherlands, Spectra® fibers, sold by Honeywell, and very high density polyethylene, and polypropylene fibers. Elastomeric fibers can be used in some cases. In some specific embodiments of the invention, the fibers are high strength materials which have a very low elongation and creep, such as aramid, liquid crystal polymer, or ultrahigh molecular weight polyethylene described in U.S. Pat. No. 5,578,374, U.S. Pat. No. 5,958,582 and/or U.S. Pat. No. 6,723,267. Fibers comprising carbon nanotubes or carbon nano-fibers may be suitable. Other carbon materials may also be suitable in some applications.

In some embodiments the fiber web may comprise multiple layers of fibers. However in other embodiments the fiber web has regions between crossings where a single fiber strand is employed to minimize the balloon profile. The strands may be manipulated to flatten as they are applied to increase the area covered by a single strand and minimize the profile of the fiber and of the overall balloon.

Friction Enhancement

To facilitate integrity of the web applied to the cone portion of the underlayer balloon, a friction-enhancing material may be provided at the interface between the underlayer balloon and the web, at least over the cone portion. The web fibers may be coated with a friction-enhancing material, or a layer of friction-enhancing material may be applied to at least the cone portion of the underlayer balloon before application of the web fibers, or both. The friction enhancing material may also be provided at the interface between the underlayer balloon and the web over other portions of the balloon, for instance over the waist and/or body portions.

The friction-enhancing material may be a polymer that has a higher coefficient of friction than either or the underlayer balloon and the fiber and which is high enough that the fibers do not substantially slip off or around on the cone during web formation. Coefficient of friction is suitably determined per ASTM D3702 against a polished steel surface and values of about 0.7 or higher are recommended, especially about 0.8 and higher. Exemplary materials may be rubbery elastomeric thermoplastic polymers, for instance, styrene-olefin block copolymers and acrylonitrile block copolymers. In some cases urethane-based thermoplastic elastomers, ester-based thermoplastic elastomers, olefin-based thermoplastic elastomers, and amide-based thermoplastic elastomers may be suitable. Linear low density polyethylene, very low density polyethylene, polyethylene-α-olefin copolymers or polycarbonate-urethane copolymers may be suitable in some cases.

One group of friction enhancers includes styrene-olefin thermoplastic elastomers. The styrene-olefin thermoplastic elastomer is a block copolymer having a soft segment and a hard segment within a molecule. The soft segment is a unit that is obtained from polymerization of an olefin, e.g., a polyisobutylene block, a polybutadiene block or a polyisoprene block. The component constituting the hard segment is a unit of styrene block, for example, that is obtained from a compound having one or at least two types selected from styrene and its derivatives, e.g., α-methyl styrene, vinyl toluene, p-tertiary butyl styrene, 1,1-diphenyl ethylene and others.

Specific examples of the styrene-olefin thermoplastic elastomers include: styrene-isobutylene-styrene block copolymer (SIBS); styrene-butadiene-styrene block copolymer (SBS); styrene-ethylene-butylene-styrene block copolymer (SEBS); styrene-isoprene-styrene block copolymer (SIS); styrene-ethylene-propylene-styrene block copolymer (SEPS); styrene-ethylene-ethylene-propylene-styrene block copolymer (SEEPS structure); and modified block copolymers thereof. The content of styrene (or its derivatives) in each of the SIBS, SBS, SEBS, SIS, SEPS and SEEPS structures is preferably in a range of 10-50 wt. %, and more preferably in a range of 15-45 wt. % within the copolymer. A particular example is SIBS with about 17 wt % styrene.

A friction-enhancing coating material may also be an adhesive. For instance, the adhesive may be one that provides at least some tack during application of the fibers. The adhesive may be a pressure sensitive, hot melt, solution, dispersion or curable material. In some embodiments of the invention, the adhesive will set up further after application of the fiber to provide an adhering bond between the fibers and the balloon which is stronger than the initial tack adhesion. Partially cured radiation curable acrylate coating materials are exemplary.

The friction-enhancing coating may be applied from a solution or dispersion. In the case of a hot melt or curable adhesive, the coating may be applied neat. Suitable coating thicknesses are from about 1 to about 25 µm, for instance from about 2 µm to about 20 µm or from about 5 to about 10 µm.

Matrix

A polymeric matrix material is applied over the web and over any exposed portions of the underlayer balloon. The matrix material should bind to the material that is at least partially exposed to the matrix material under the particular technique employed. The exposed material may be one or more of the web fiber material, the underlayer balloon and, if employed, the friction enhancing material. The matrix material may be the same or similar to the friction-enhancing material. The matrix material may also be the same or similar to the bulk material of the underlayer balloon, or it may be a wholly different material from both the friction-enhancing material and the underlayer balloon material. The matrix material in some embodiments is heat activatable, i.e. after application adhesive properties can be activated by heating.

The matrix material may be applied from solvent or dispersion. In some cases a curable liquid which sets up after application may be employed as matrix material. The matrix material may also be applied from the melt, for instance by spraying or extruding over the web.

Examples of matrix materials which may be employed include the styrene-olefin thermoplastic elastomers already described. Polyurethanes, for instance silicone modified polyurethanes may be employed. UV curable compositions as described in more detail in US 2006-0008606 A1 may also be employed.

A solution or dispersion or a polymer formulation having hot-melt adhesive properties, i.e. one that after drying may still be activated with heat to bond to a subsequently applied substrate, may be used.

In some embodiments the matrix material and the friction-enhancing material, in combination, also bind the filaments of the fibrous material to the underlayer balloon.

Outerlayer Balloon

An outerlayer balloon is positioned over the assembly of underlayer balloon, fiber web and matrix material to form a composite balloon.

The outerlayer balloon is a thin molded balloon and may be preformed in a manner known for forming medical device balloons, for instance by any of the means described herein for forming the underlayer balloon. The materials of the outer layer balloon may be selected from the same materials already identified for the underlayer balloon. The material of the outer layer balloon may be the same or different from that of the underlayer balloon.

The outerlayer balloon is formed with an inner diameter which will receive the underlayer balloon and web matrix combination. In some embodiments, the outerlayer balloon is radially oriented or biaxially (radially and longitudinally) oriented.

The outer layer balloon may have any suitable wall thickness. In some embodiments, the wall thickness may be comparable to that of the underlayer balloon, for example, on single wall basis from about 5 µm to about 50 µm (0.0002-0.002 inches), for instance from about 8 to about 30 µm (0.0004-0.0012 inches), suitably from about 10 to about 25 µm (0.0004-0.0010 inches).

Forming the Composite Balloon

The combination of the above described layers, as mentioned above, forms a composite balloon that is flexible and has high strength and a high burst pressure. In forming the composite balloon, the underlayer balloon 122 can be formed and molded using a conventional molding process. The molded underlayer balloon may then be inflated and both ends sealed. The underlayer balloon 122 optionally may then be coated with a friction enhancing material 124, such as a pressure sensitive adhesive. The fiber web 126 is then applied to the surface of the underlayer balloon 122, suitably as a braid of fibers of Spectra® or Vectran® materials, or the like. The fiber web 126 is then encased with matrix material 128. As a particular example a solution or dispersion or a polymer formulation having hot-melt adhesive properties upon drying may be used.

After any solvent is dried off, the pressure is released. The assembly of the underlayer balloon 122, fiber web 126 and matrix 128 is then inserted into a previously formed outerlayer balloon 140. The outerlayer balloon 140 may be slightly larger than the underlayer balloon 122 or it may have the same dimensions. The proximal and distal waist of the outerlayer balloon 140 may be larger than those of the underlayer balloon 122 to ease insertion.

After insertion, the combination balloon is inflated and heated at a temperature above the temperature at which the underlayer and outer layer balloons were formed. For instance if the underlayer and outer layer balloons are blown at a temperature in the range of about 90° C. to about 100° C., a heat temperature in the range of from about 110° to about 130° may be employed, for instance about 115° C. A suitable heat time may be from about 15 seconds to about 5 minutes, for instance about one minute. The heated inflation pressure is suitably about the same or higher pressure than the pressure at which the underlayer balloon or the outer layer balloon, whichever was higher, for example the range of 40-50 psi. During heating the matrix material desirably is activated to adhere to the outerlayer balloon to laminate the layers together.

In some embodiments, the heat set temperature is set by the adhesive activation temperature instead of higher than the balloon molding temperature.

In general the conditions for formation of the underlayer and outer layers may be substantially the same so that they will have similar behavior during heating. However, in some cases it may be advantageous for the underlayer and outer layer balloons to have been formed at different temperature and or pressure conditions such that the outer layer balloon shrinks slightly during heating while the underlayer balloon remains unchanged or expands slightly. Such technique may increase the bonding pressure of the outer layer balloon to the adhesive matrix material and assist in flattening fiber strands therebetween so to further minimize the total balloon thickness.

Although it should be understood that in some embodiments there is no coating on the outerlayer balloon, the composite balloon may have a coating of a lubricous material or which comprises drug, as is generally known. See, for instance U.S. Pat. No. 5,135,516; U.S. Pat. No. 5,026,607; U.S. Pat. No. 5,304,121; U.S. Pat. No. 5,576,072; U.S. Pat. No. 5,503,631; U.S. Pat. No. 5,509,899; U.S. Pat. No. 5,693,034; U.S. Pat. No. 6,110,483; U.S. Pat. No. 5,702,756; U.S. Pat. No. 6,528,150; and U.S. Pat. No. 6,673,053.

The composite balloon may have a single wall thickness of about 50 to about 250 µm, suitably about 50 to about 230 µm. In some embodiments, the single wall thickness of about 50 to about 80 µm with a target at 60 µm.

Wall strengths for such balloons may be in excess of about 15,000 psi (103,421 kPa), typically at least about 18,000 psi (124,106 kPa), and in most cases in the range of about 25,000 to about 40,000 psi. Balloon diameters may range from about 1.5 to about 14 mm. The resulting composite balloons also exhibit repeat inflation durability and strength. In testing, composite balloons of the present invention passed 100 cycles at 20 ATM.

Fiber-Matrix/Balloon Thickness Ratio

In some aspects the invention relates to the particular ratio of fiber and matrix material employed relative to the overall balloon thickness.

Referring now to FIG. 5, the wall 142 of the composite balloon has an overall thickness 144, referred to as the composite balloon wall thickness 144, and a thickness 146 of the combination of the fiber web 126 and matrix material 128, referred to as the fiber matrix thickness 146. In order to minimize the profile of the medical balloon, while at the same time maintain a high burst pressure, the present invention also contemplates minimizing the thickness of the fiber strands used to form the fiber web. To achieve this reduced fiber size, the yarn that makes up the fiber web 126 is desirably manipulated to spread out as it is applied so as to cover a greater area.

To measure the effect of fiber spreading, a fiber matrix ratio (R) is established. The ratio (R) reflects the relative thickness of the fiber and matrix material layer, compared to the total balloon thickness at a location where a single strand of fiber lies between the under and outer layers. Referring again to FIG. 3, R is taken as the thickness 146 divided by the composite balloon wall thickness 144.

The fiber matrix ratio may be suitably calculated based on 30 random measurements to determine total thickness. The fiber matrix is calculated using a scanning electron microscope or some other suitable device. The sample thickness is measured over a 10 mm squared area.

The inventors of the present invention have found that the fiber matrix ratio is an effective tool in optimizing the balance between minimizing profile while maintaining high burst pressure for fiber reinforced balloon. In some embodiments, fiber reinforced balloons having an R value of between about 0.51 and about 0.73 have been found to exhibit favorable characteristics.

The following examples illustrate the invention in preliminary, non-optimized trials.

Example

Underlayer balloons were prepared by radial expansion of extruded tubes of Pebax® 7233 polymer. The underlayer balloons had an average double wall thickness in the body region of approximately 0.0016 inches, a molded diameter of approximately 8 mm and a molded body length of approximately 2 cm. The underlayer balloons were sterilized with ethylene oxide according to a conventional protocol. At this stage, three balloons were retained, unbraided, as controls for comparison purposes.

The underlayer balloons were heat-sealed at their distal end. The proximal end was connected to a pneumatic syringe and pressurized balloon component to a firm stiffness (1-2 atm internal pressure).

A coating of pressure sensitive adhesive, HL-2081 from H.B. Fuller, was applied to the exterior surface of the underlayer balloon by hand dipping the pressurized balloon component into a solution of 25% adhesive in Toluene, drawing the balloon component out of solution and allowing it to dry.

A braiding machine was utilized to weave a web of fibers of 50 denier fiber form Dyneema from DSM around the inflated balloon components. Speeds were adjusted as braiding progressed in a manner directed to achieve a single layer braiding with an estimated 68-70 degree braiding angle.

The pressurized balloon component was then dipped into a solution of 10% hot melt HM-0230 in toluene, drawing the balloon component out of solution and letting it thoroughly dry.

Overlayer balloons of Pebax® 7233 polymer were prepared in the same manner and with the same dimensions as the underlayer balloons.

Resulting balloons made from the above process had a fiber matrix ratio of 0.73 and an average burst of 30 ATM.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. An expandable medical balloon comprising:
   an underlying balloon layer comprising a thermoplastic elastomer, the underlying balloon layer is biaxially oriented;
   a friction enhancing layer disposed on at least a portion of an outer surface of the underlying balloon layer, the friction enhancing layer comprises a thermoplastic polyurethane;
   a fiber web disposed on the underlying balloon layer and disposed on the friction enhancing material, the fiber web comprises an aromatic polyester; and
   an overlying balloon layer comprising a thermoplastic elastomer, the thermoplastic elastomer comprises a thermoplastic polyurethane.

2. The expandable medical balloon of claim 1 wherein the underlying balloon layer has a wall thickness of about 5 microns to about 50 microns.

3. The expandable medical balloon of claim 1 wherein the underlying balloon layer has a thickness of about 10 microns to about 25 microns.

4. The expandable medical balloon of claim 1 wherein the underlying balloon layer has a thickness of about 15 microns.

5. The expandable medical balloon of claim 1 wherein ratio of the thickness of the underlying balloon layer to overlying balloon layer is about 3:1 to about 5:1.

6. The expandable medical balloon of claim 4 wherein the ratio of the thickness of the underlying balloon layer to the overlying balloon layer is about 3.5:1.

7. The expandable medical balloon of claim 1 wherein the underlying balloon layer has a shore D hardness of about 70.

8. The expandable medical balloon of claim 1 wherein the expandable medical balloon has an actual burst strength of about 30 ATM.

9. The expandable medical balloon of claim 1 wherein the underlying balloon layer comprises polyether-block-amide.

10. An expandable medical balloon comprising:
    an underlying balloon layer comprising a thermoplastic elastomer, the underlying balloon layer is biaxially oriented;
    a friction enhancing layer disposed on at least a portion of an outer surface of the underlying balloon layer, the friction enhancing layer comprises a thermoplastic polyurethane;
    a fiber web disposed on the underlying balloon layer and disposed on the friction enhancing material, the fiber web comprises an aromatic polyester; and
    an overlying balloon layer comprising a thermoplastic elastomer, the thermoplastic elastomer comprises a thermoplastic polyurethane;
    wherein a ratio of thickness of the underlying balloon layer to the overlying balloon layer is about 3:1 to about 5:1.

11. The expandable medical balloon of claim 10 wherein the underlying balloon layer has a wall thickness of about 5 microns to about 50 microns.

12. The expandable medical balloon of claim 10 wherein the underlying balloon layer has a thickness of about 10 microns to about 25 microns.

13. The expandable medical balloon of claim 10 wherein the underlying balloon layer has a thickness of about 15 microns.

14. The expandable medical balloon of claim 10 wherein the ratio of the thickness of the underlying balloon layer to the overlying balloon layer is about 3.5:1.

15. The expandable medical balloon of claim 10 wherein the ratio of the thickness of the underlying balloon layer to the friction enhancing layer is about 3:1 to about 5:1.

16. An expandable medical balloon comprising:
- an underlying balloon layer comprising a polymer material, the underlying balloon layer is biaxially oriented;
- a friction enhancing layer disposed on at least a portion of an outer surface of the underlying balloon layer, the friction enhancing layer comprises a thermoplastic polyurethane;
- a fiber web disposed on the underlying balloon layer and disposed on the friction enhancing material, the fiber web comprises an aromatic polyester; and
- an overlying balloon layer comprising a thermoplastic elastomer, the thermoplastic elastomer comprises a thermoplastic polyurethane.

17. The expandable medical balloon of claim 16 wherein the underlying balloon layer comprises polyether-block-amide, polyamide, or a combination thereof.

\* \* \* \* \*